(12) United States Patent
Sharma

(10) Patent No.: US 10,160,544 B2
(45) Date of Patent: *Dec. 25, 2018

(54) AIRCRAFT OCCUPANT HEALTH, SAFETY, AND COMFORT MANAGEMENT

(71) Applicant: AIRBUS GROUP INDIA PRIVATE LIMITED, Bangalore (IN)

(72) Inventor: Anurag Sharma, Bangalore (IN)

(73) Assignee: AIRBUS GROUP INDIA PRIVATE LIMITED, Bangalore, Karnataka (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/250,952

(22) Filed: Aug. 30, 2016

(65) Prior Publication Data

US 2017/0066534 A1    Mar. 9, 2017

(30) Foreign Application Priority Data

Sep. 9, 2015  (IN) .......................... 4790/CHE/2015
Oct. 26, 2015 (IN) .......................... 5733/CHE/2015

(51) Int. Cl.
```
B64D 11/06      (2006.01)
B64D 11/00      (2006.01)
A61B 5/083      (2006.01)
A61B 5/11       (2006.01)
A61B 5/00       (2006.01)
```

(52) U.S. Cl.
CPC .............. *B64D 11/06* (2013.01); *A61B 5/083* (2013.01); *A61B 5/11* (2013.01); *A61B 5/746* (2013.01); *B64D 11/0015* (2013.01); *B64D 11/0626* (2014.12)

(58) Field of Classification Search
CPC .............. G08B 21/0461; B64D 11/062; B64D 11/0626; A61B 5/0816; A61B 5/6891; A61M 21/02
USPC ................ 340/573.1, 945, 665–668, 539.12
See application file for complete search history.

(56) References Cited

U.S. PATENT DOCUMENTS

| | | | |
|---|---|---|---|
| 5,724,371 A * | 3/1998 | Magne | H01S 3/0675 372/102 |
| 7,183,930 B2 * | 2/2007 | Basir | A61B 5/02455 340/521 |
| 7,482,938 B2 * | 1/2009 | Suzuki | B60N 2/002 340/425.5 |

(Continued)

*Primary Examiner* — Eric M Blount
(74) *Attorney, Agent, or Firm* — Prakash Nama; Global IP Services, PLLC

(57) ABSTRACT

An aircraft occupant health, safety, and comfort management is disclosed. In one embodiment, an aircraft occupant, seated in an aircraft occupant seat in an aircraft, substantially around the aircraft occupant seat is monitored for health, safety and comfort information using at least one sensor disposed in the aircraft occupant seat and/or substantially around the aircraft occupant seat. Further, background auditory, electrical noise, temperature and mechanical vibration associated with the aircraft occupant seat is measured using the at least one sensor. The health, safety and comfort information associated with the aircraft occupant is then obtained using the monitored health safety and comfort information and the measured background electrical noise and mechanical vibration. Health, safety and comfort of the aircraft occupant are then managed based on the obtained health, safety and comfort information.

24 Claims, 5 Drawing Sheets

(56) References Cited

U.S. PATENT DOCUMENTS

| | | | | |
|---|---|---|---|---|
| 7,650,803 | B2* | 1/2010 | Ando | A61B 5/103 |
| | | | | 73/862.391 |
| 7,932,837 | B2* | 4/2011 | Giesa | B60R 22/48 |
| | | | | 244/122 R |
| 8,941,499 | B2* | 1/2015 | Fung | A61B 5/6893 |
| | | | | 340/425.5 |
| 9,468,388 | B2* | 10/2016 | Nishii | A61B 5/6891 |
| 9,589,106 | B2* | 3/2017 | Bangera | G06F 19/345 |
| 9,864,842 | B2* | 1/2018 | Hyde | G16H 20/13 |
| 2001/0048071 | A1* | 12/2001 | Holz | G01D 5/35383 |
| | | | | 250/227.12 |
| 2006/0187015 | A1* | 8/2006 | Canfield | H04B 3/548 |
| | | | | 340/474 |
| 2008/0015753 | A1* | 1/2008 | Wereley | B60N 2/4242 |
| | | | | 701/45 |
| 2008/0103368 | A1* | 5/2008 | Craine | A61B 5/0002 |
| | | | | 600/300 |
| 2010/0036209 | A1* | 2/2010 | Ferren | A61B 5/0002 |
| | | | | 600/301 |
| 2013/0069630 | A1* | 3/2013 | Manson | G01L 9/08 |
| | | | | 324/109 |
| 2013/0070043 | A1* | 3/2013 | Geva | B60K 28/066 |
| | | | | 348/14.02 |
| 2013/0338857 | A1* | 12/2013 | Sampigethaya | A61B 5/6887 |
| | | | | 701/3 |
| 2014/0039330 | A1* | 2/2014 | Seo | A61B 5/0452 |
| | | | | 600/509 |
| 2015/0133804 | A1* | 5/2015 | Sugiyama | A61B 5/0408 |
| | | | | 600/509 |
| 2015/0313475 | A1* | 11/2015 | Benson | A61B 5/6893 |
| | | | | 297/217.3 |
| 2016/0320219 | A1* | 11/2016 | Hellevang | G01F 1/66 |
| 2016/0354027 | A1* | 12/2016 | Benson | A61M 21/02 |

* cited by examiner

AIRCRAFT OCCUPANT HEALTH, SAFETY, AND COMFORT MANAGEMENT

CROSS-REFERENCE TO RELATED APPLICATIONS

This application claims priority to Indian Application Number 4790/CHE/2015 filed on Sep. 9, 2015, entitled "AIRCRAFT OCCUPANT SEAT FOR AIRCRAFT OCCUPANT HEALTH, SAFETY, AND COMFORT MANAGEMENT" and 5733/CHE/2015 filed on Oct. 26, 2015, entitled "AIRCRAFT OCCUPANT HEALTH, SAFETY AND COMFORT MANAGEMENT" by AIRBUS GROUP INDIA PRIVATE LIMITED which is herein incorporated in its entirety by reference for all purposes.

TECHNICAL FIELD

Embodiments of the present subject matter generally relate to vehicle occupant health, safety, and comfort management, and more particularly, to aircraft occupant health, safety and comfort management.

BACKGROUND

Aircraft manufacturers, airlines and other operators of commercial and other aircraft may recognize the desirability of being able to cater to the health, safety and comfort of aircraft occupants. As a result, aircraft may be designed to include various systems and aircraft operators may also provide various services that are intended to support the health, safety and comfort of aircraft occupants.

For example, aircraft may include equipment for monitoring and controlling environmental conditions in an aircraft cabin. In some aircraft, equipment may be provided that allows passengers to adjust environmental conditions at their own seats in the aircraft cabin to some degree. Airlines may also provide various services for supporting the health, safety and comfort of occupants of an aircraft. For example, an airline may provide an in-flight food service, seat/headrest position and temperature control and so on. Many current commercial and other aircraft may include equipment that may allow the occupants of the aircraft to provide an on-demand response to medical emergencies on the aircraft.

However, with the current systems and services, occupant's health, safety and comfort may be hard to evaluate and advance warning of any potential degradation/long term monitoring to prevent incidents is not possible and it may be even harder to provide a tailored wellbeing to each aircraft occupant as each occupant may respond differently to an aircraft environment based on their health, emotional and physical state, such as whether they are fatigued and/or having medical problems. Further, while on board, aircraft occupants may experience serious medical conditions, and in such scenarios, due to lack of attention, assistance and/or medical help, may result in occupant fatalities. This may also result in diversions of missions and losses during operation due to crew member's inability to determine the seriousness of the aircraft occupant's health. Furthermore, monitoring and providing needed comfort to each occupant during flight may pose another challenge.

SUMMARY

A system for aircraft occupant health, safety, and comfort management is disclosed. According to one aspect of the present subject matter, an aircraft occupant, seated in an aircraft occupant seat in an aircraft, substantially around the aircraft occupant seat is monitored for health, safety, alertness/sleepiness, and comfort information using at least one sensor disposed in the aircraft occupant seat and/or substantially around the aircraft occupant seat. Further, background electrical noise and mechanical vibration associated with the aircraft occupant seat is measured using the at least one sensor. The health, safety and comfort information associated with the aircraft occupant is then obtained using the monitored health, safety, and comfort information and the measured background electrical noise and mechanical vibration. Health, safety and comfort management of the aircraft occupant are then managed based on the obtained health, safety and comfort information. Alerts can then be provided to the crew members, off board aircraft occupant medical monitoring facility via satellite, and ground station computing system to prevent deterioration via early warning systems/long term health trend monitoring.

According to another aspect of the present subject matter, the system may include an aircraft occupant seat that may include an aircraft occupant health, safety and comfort management system. Further, the aircraft occupant health, safety and comfort management system may include at least one processor, a network interface card to communicatively coupled to an aircraft network data processing system residing in an aircraft, at least one sensor disposed in the aircraft occupant seat, and a storage device coupled to the at least one processor. Furthermore, the storage device may include an aircraft occupant health, safety and comfort management module (AOHSCMM) to perform the method described above. In addition, the system may include cabin environmental systems, cabin display, cabin condition sensors and an aircraft network data processing system that is communicatively coupled to the cabin environmental systems, cabin display, and cabin condition sensors. Moreover, the system may include a ground station computing system and aircraft occupant medical monitoring facility that are communicatively coupled to the aircraft network data processing, system via a satellite or other data links.

The system and method disclosed herein may be implemented in any means for achieving various aspects. Other features will be apparent from the accompanying drawings and from the detailed description that follow.

BRIEF DESCRIPTION OF THE DRAWINGS

Various embodiments are described herein with reference to the drawings, wherein.

DETAILED DESCRIPTION

A system and method for providing aircraft occupant health, safety and comfort management are disclosed, in the following detailed description of the embodiments of the present subject matter, references are made to the accompanying drawings that form a part hereof, and in which are shown by way of illustration specific embodiments in which the present subject matter may be practiced. These embodiments are described in sufficient detail to enable those skilled in the art to practice the present subject matter, and it is to be understood that other embodiments may be utilized and that changes may be made without departing from the scope of the present subject matter. The following detailed description is, therefore, not to be taken in a limiting sense, and the scope of the present subject matter is defined by the appended claims.

Embodiments described herein provide systems and methods for aircraft occupant health, safety, comfort management and long term monitoring by ground station computing system and aircraft occupant medical monitoring facility via a satellite. The example technique disclosed herein significantly reduces manpower for providing aircraft occupant health, safety and comfort. Further the systems and methods described herein may reduce unnecessary diversions and may direct the flight to a nearest available facility for managing aircraft occupant health, safety and comfort or facilitate remote assistance. Furthermore, the systems and methods may utilize best available medical practices when a physician is not on board the aircraft, in addition, the systems and methods may significantly reduce chances of losing the aircraft when a pilot is medically incapacitated or long term monitoring trends may suggest that a medical emergency may be imminent. Also, the systems and methods may facilitate in recognizing a situation & transferring the control of the aircraft to another pilot or ground station in case the pilot is incapacitated. Moreover, the systems and methods may send alerts in case of non-compliance of aircraft occupant health safety, security and comfort. In addition, the systems and methods described herein may utilize expert medical opinion even when a doctor is not present on board by using an off board aircraft occupant medical monitoring facility. Also, the systems and methods may transfer control to ground station via a satellite or data link in case a pilot is incapacitated while operating the aircraft. Furthermore, the systems and methods may send alerts to vehicle systems in case of non-compliance of aircraft occupant safety/health during operation and while on board the aircraft.

Figure 1:
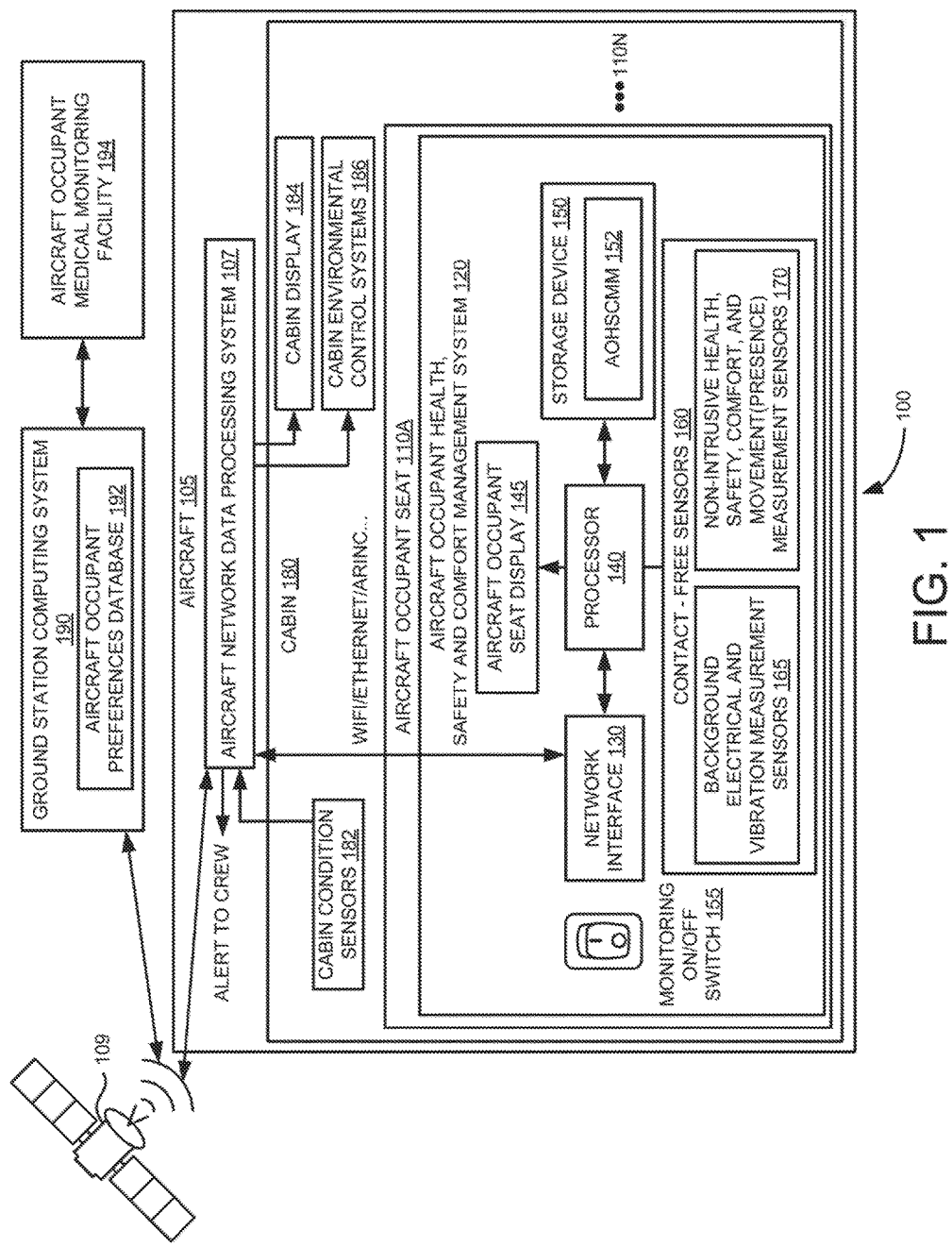
FIG. 1 is a block diagram illustrating a system for aircraft occupant health, safety and comfort management, according to an embodiment.

Referring now to FIG. 1, which is a block diagram 100 illustrating an exemplary system including an aircraft 105, a satellite 109 (for example, communication means air-ground receivers, data links and the like), a around station computing system 190, and an aircraft occupant medical monitoring facility 194 that are communicatively coupled with each other. As shown in FIG. 1, the ground station computing system 190 may include an aircraft occupant preferences database 192. Further as shown in FIG. 1, the aircraft 105 may include an aircraft network data processing system 107 that is communicatively coupled to the ground station computing system 190 via the satellite 109. The terms "aircraft network data processing system 107" and "an aircraft network and communication system" may be used interchangeably throughout the document. In addition, as shown in FIG. 1, the aircraft 105 includes a cabin 180. Also as shown in FIG. 1, cabin 180 includes cabin condition sensors 182, cabin display 184, cabin environmental control systems 186 and aircraft occupant seats 110 A-N including an aircraft occupant health, safety and comfort management system 120 in each seat for managing health, safety and comfort of an aircraft occupant seated in the aircraft occupant seat 110A-N in the aircraft 105. The term "aircraft occupant" refers to anyone seated in the aircraft, such as pilot, passenger, cabin-crew and the like. As shown in FIG. 1, the aircraft occupant health safety and comfort management system 120 includes a network interface 130 to couple to the aircraft network data processing system 107 disposed in the aircraft 105. Further as shown in FIG. 1, the aircraft occupant health, safety, and comfort management system 120 includes a processor 140 coupled to the network interface 130, a storage device 150 coupled to the processor 140, contact-free sensors 160 coupled to the processor 140, and an aircraft occupant seat display 145 coupled to the processor 140. Also as shown in FIG. 1, contact-free sensors 160 include background electrical noise and vibration measurement sensors 165 and non-intrusive health, safety, comfort, and movement measurement sensors 170.

In addition, the aircraft occupant health, safety and comfort management system 120 includes a monitoring on/off switch 155, which may be used by an aircraft occupant to turn on and off the aircraft occupant health safety and comfort management system 120. Further, the monitoring on/off switch 155 may be configured to turn on/off personal information associated with the aircraft occupant and not the information associated with security and safety. For example, not providing ability to the aircraft occupant for switching off the alerts on removal of lifejacket and/or oxygen mask or seatbelt from the aircraft occupant seat 110 A-N.

In addition, as shown in FIG. 1, the network interface 130 is communicatively coupled to the aircraft network data processing system 107 via WIFI, ETHERNET, ARINC, and the like. Moreover, as shown in FIG. 1, the aircraft 105 includes a cabin display 184 coupled to the aircraft network data processing system 107. Furthermore, as shown in FIG. 1, aircraft occupant/passenger preferences database 192 is coupled to the aircraft network data processing system 107 via the satellite 109. Even though the idea is described with reference to using, satellite for communicating between aircraft to ground communication channel, one can envision using other aircraft to ground communication channels, such as gatelink/ground internet transponders which can communicate while aircraft is over land (for example, Go-Go internet) and the like.

Figure 2:
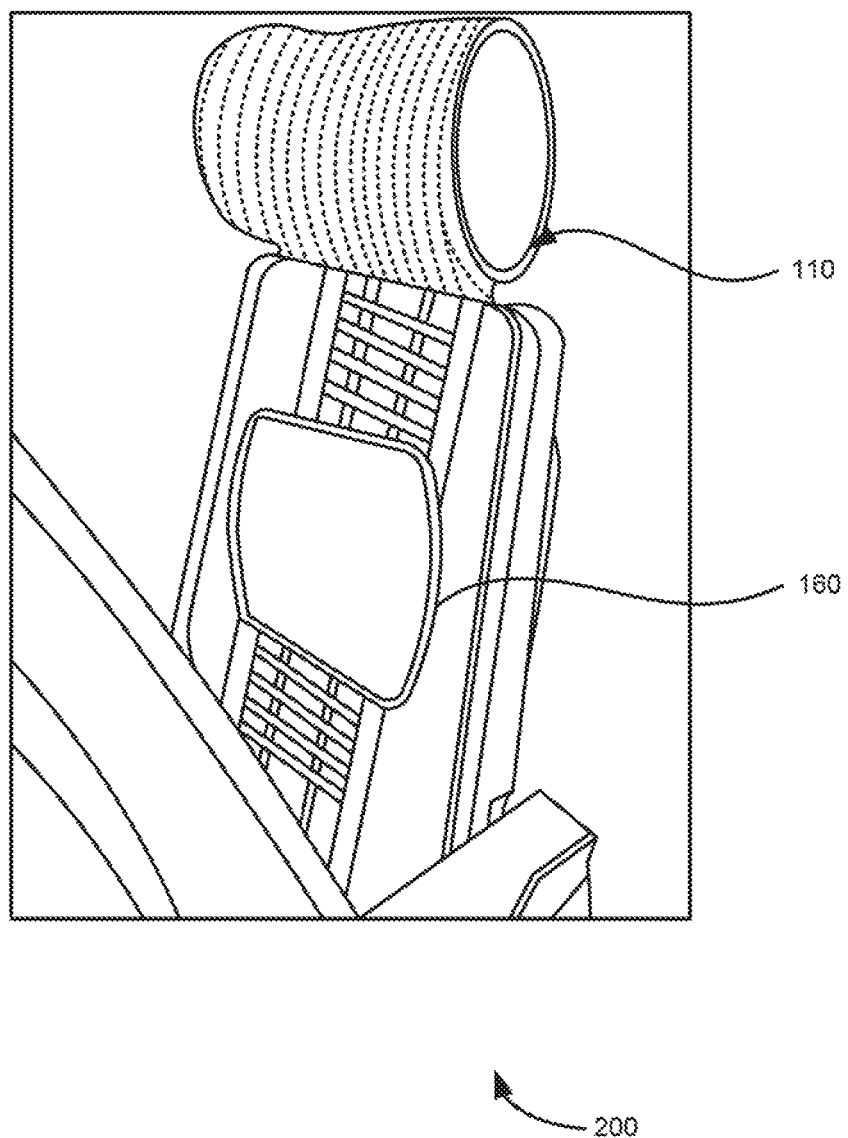
FIGS. 2 and 3 are schematic diagrams showing example dispositions of the contract-free piezo-electric sensors in an aircraft occupant seat for aircraft occupant health, safety and comfort management, according to an embodiment.
Figure 3:
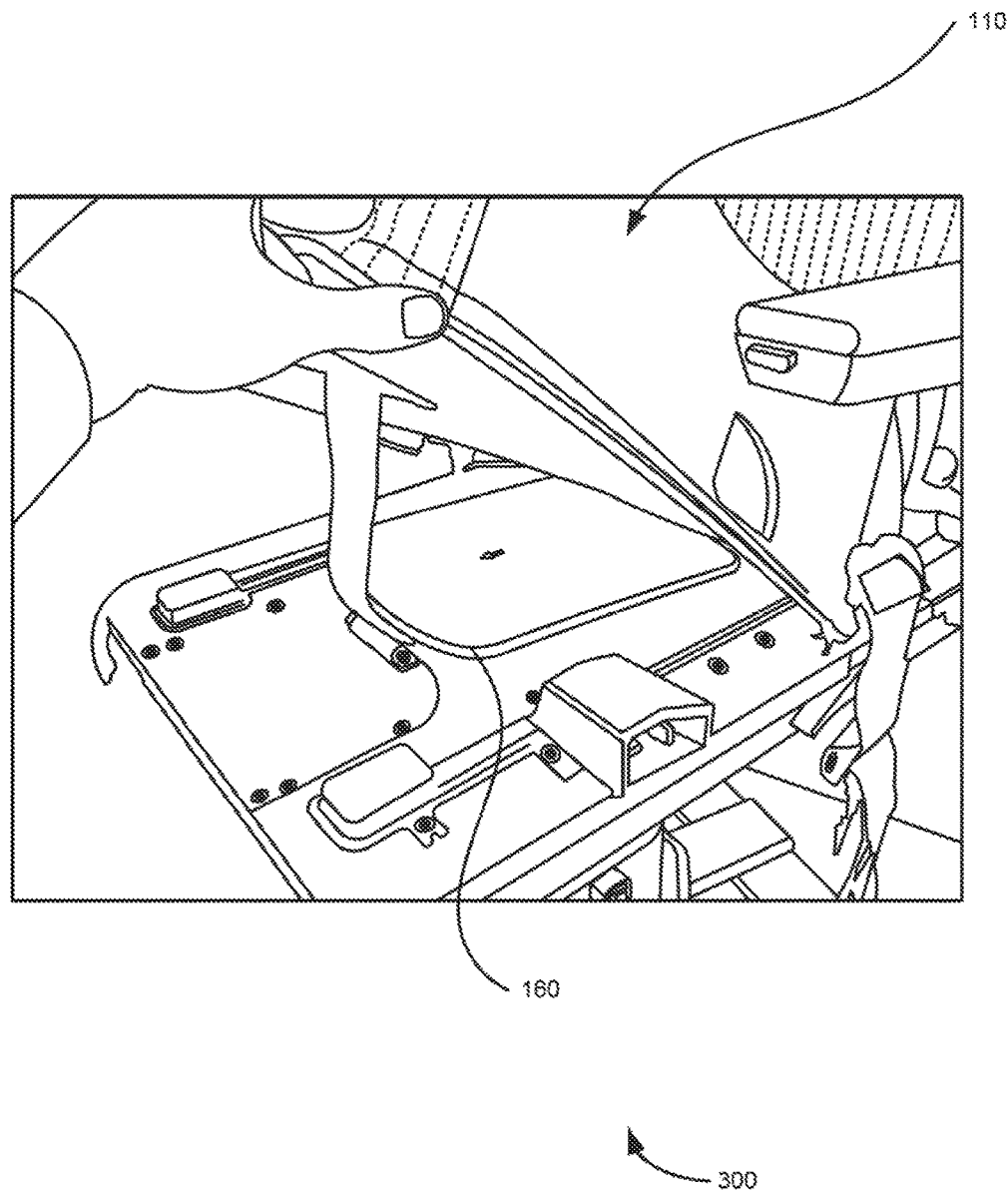
Figure 4:
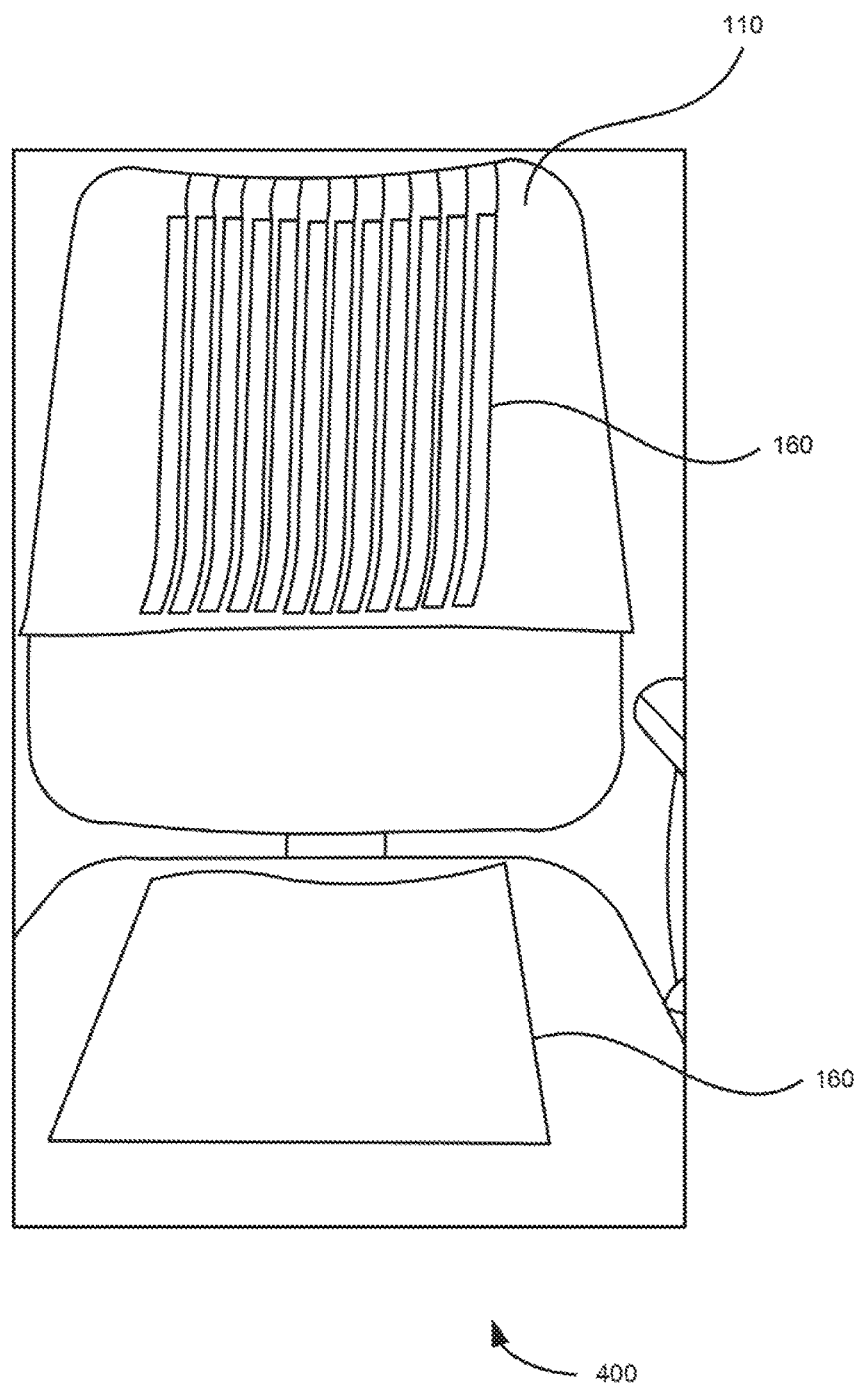
FIG. 4 is a schematic diagram showing example disposition of electro-potential EKG and ECG sensors (i.e., fabric embedded electrode wires) in the aircraft occupant seat cover on the seatback or headrest for aircraft occupant health, safety and comfort management, according to an embodiment.

In operation, aircraft occupant health, safety and comfort management module (AOHSCMM) 152 along with the aircraft network data processing system 107 monitors an aircraft occupant, seated in the aircraft occupant seat 110A in the aircraft 105, substantially around the aircraft occupant seat 110A for health, safety and comfort information using at least one sensor 160 disposed in the aircraft occupant seat 110A and the cabin condition sensors 182 disposed substantially around the aircraft occupant seats 110A-N. Example at least one sensor is a contact free sensor and/or a non-intrusive sensor. Further example, at least one sensor is a piezoelectric sensor, electrometer (electric potential measurement sensor), optical fiber Bragg grating sensor, and/or cabin condition sensor 182. In FIGS. 2 and 3, the examples 200 and 300 shown are a contact-free sensor 160 disposed in the aircraft occupant seats 110A-N. It can be seen that the contact-free sensor 160 may be disposed in the aircraft occupant seats 110 A-N to accommodate varying sizes and positions of the aircraft occupants. Further, the cabin condition sensors 182 may be disposed substantially around the aircraft occupant seats 110 A-N and may be part of the aircraft air-conditioning systems which communicate with the aircraft occupant seat 110 A-N via the aircraft-seat interface. The cabin condition sensors 182 may be used for measuring ambient condition around the aircraft occupant seated in one or more the of aircraft occupant seats 110 A-N. In the example shown in FIGS. 2 and 3, the piezoelectric sensor may be disposed below or behind the seat cushion of the aircraft occupant seats 110 A-N. Further in the example shown in FIG. 4, the electro-potential sensors 160 are disposed on the surface and/or integrated as part of the aircraft occupant seat cover. One can envision that the electro-potential sensors 160 can be disposed in the aircraft occupant seat and/or the headrest to measure alpha/beta brain activity to check sleep level (i.e., rapid eye movement (REM)/Non REM sleep). For example, REM sleep may occur when a person is dreaming, and in such a scenario coordinating the blue/green light at the end of last REM phase after a rest period of few hours may be very effective to the aircraft occupant in alleviating jetlag.

In one example embodiment, the non-intrusive health safety, comfort, and movement sensor 170 is used for measuring vital signs of the aircraft occupant. Further in another example embodiment, non-intrusive health, safety, comfort, and movement sensor 170 is used for measuring chest muscle movement (i.e., for measuring heart/pulse rate and breathing rate), sense pulse via ballistocardiogram (BCG), and wakefulness/sleep level of the aircraft occupant. For example, the non-intrusive health, safety, comfort, and movement sensor 170 disposed in the bottom of the aircraft occupant seat may be configured to sense heart rate and breathing, rate by body recoil (i.e., ballistogcardiagram)

Further in operation, the AOHSCMM 152 measures background electrical noise and mechanical vibration associated with the aircraft occupant seat 110 using the at least one sensor 160. Furthermore in operation, the AOHSCMM 152 along with the aircraft network data processing system 107 obtains the health safety and comfort information associated with the aircraft occupant using the monitored health safety and comfort information and the measured background electrical noise, mechanical vibration, and cabin condition.

In addition in operation, the AOHSCMM 152 along with the aircraft network data processing system 107 manages health, safety and comfort of the aircraft occupant based on the obtained health, safety and comfort information. Example health, safety and comfort management of the aircraft occupant includes adjusting airflow vent/air conditioner temperature substantially around the occupant seat based on stored preferences and/or occupant selection or activity levels, providing ability to obtain waiting position number for the washroom and informing the aircraft occupant about availability of washroom upon reaching the obtained waiting position number, notifying seat belt condition to the aircraft cabin crew, providing blue/green light to awake the aircraft occupant, providing an optimized seating position to the aircraft occupant, providing seat presence or absence signal to cabin crew, switching off audio/pausing the in flight entertainment system on detecting sleep, providing appropriate audio level to the aircraft occupant, providing ambient noise cancellation or white noise to the occupant, providing appropriate refreshments to the aircraft occupant, providing emergency equipment condition information to the cabin crew, and/or providing condition of personal electronic equipment connected to the aircraft occupant based on the obtained health, safety and comfort information.

Also in operation, the AOHSCMM 152 along with the aircraft network data processing system 107 may send an alert to crew by displaying the health, safety and comfort information on the aircraft occupant seat displays 145 and/or cabin display 184 via the aircraft network data processing system 107 based on the obtained health, safety and comfort information. Moreover, in operation, the AOHSCMM 152 along with the aircraft network data processing system 107 may send an alert to other aircraft occupants residing in the cabin, send the alert to off board aircraft occupant medical monitoring facility via, satellite/ground station 109/190 based on the obtained health, safety and comfort information, and/or send obtained health, safety and comfort information to crew or off board aircraft occupant medical monitoring facility 184 based on phase of operation of aircraft via aircraft to ground channels or via satellite 109.

Further in operation, one can envision configuring AOHSCMM 152 to provide the ability to warn about removal of flight safety equipment from the aircraft occupant seat 110A to cabin-crew (For example, removal of oxygen mask or life jacket) so cabin-crew can prevent removal at disembarkation). Furthermore in operation, configuring AOHSCMM 152 to provide ability to decide where to route the alerts during different flight phases. For example, if a passenger is ill before takeoff, both the pilot and the cabin crew may be alerted. Further for example, if during takeoff and/or landing only cabin crew may be alerted. Also for example, during flight displaying the seat belt or tray table alert/reminder to occupant or cabin crew when not complied.

Furthermore in operation, the aircraft network data processing system 107 may be configured to receive instructions from the off board aircraft occupant medical monitoring facility 194 via satellite/around station 109/190 to manage health, safety, and/or comfort of the aircraft occupant. Example instructions received from the aircraft occupant medical monitoring facility 194 may include at least one of first aid instructions, prescription information, and suggesting landing the aircraft.

Figure 5:
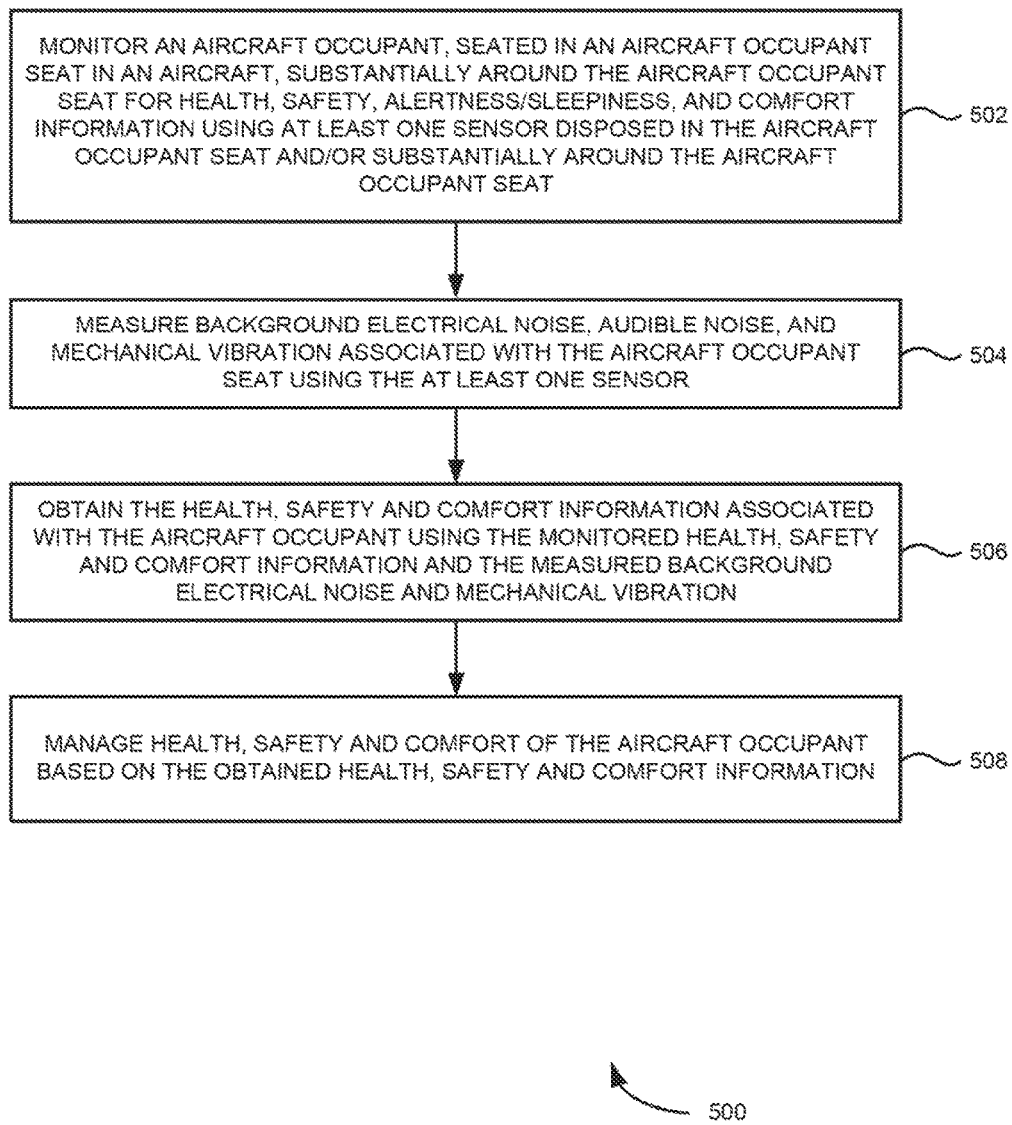
FIG. 5 is a flowchart illustrating a process for aircraft occupant health, safety and comfort management, according to an embodiment.

Referring now to FIG. 5, which illustrates a flow diagram 500 of an exemplary method for aircraft occupant health, safety and comfort management. At block 502, an aircraft occupant, seated in an aircraft occupant seat in an aircraft, substantially around the aircraft occupant seat is monitored for health, safety, alertness/sleepiness, and comfort information using at least one sensor disposed in the aircraft occupant seat and/or substantially around the aircraft occupant seat. At block 504, background electrical noise, audible noise, and/or mechanical vibration associated with the aircraft occupant seat is measured using the at least one sensor. At block 506, the health, safety and/or comfort information associated with the aircraft occupant is obtained using the monitored health, safety and comfort information and the measured background electrical noise and mechanical vibration. At block 508, health, safety and comfort of the aircraft occupant is managed based on the obtained health, safety and comfort information. Further, an alert is sent to crew/ground station or displaying the health, safety and comfort information on a display device based on the obtained health, safety and comfort information. This method is explained in more detail with reference to FIG. 1 and FIGS. 2-4.

Although the present embodiments have been described with reference to example embodiments, it will be evident that various modifications and changes may be made to these embodiments without departing from the broader spirit and scope of the various embodiments. Furthermore, the various devices, modules, analyzers, venerators, and the like described herein may be enabled and operated using hardware circuitry, for example, complementary metal oxide semiconductor based logic circuitry, firmware, software and/or any combination of hardware, firmware, and/or software embodied in a machine readable medium. For example, the various electrical structure and methods may be embodied using transistors, logic gates, and electrical circuits, such as application specific integrated circuit.

What is claimed is:

1. A method for aircraft occupant health, safety and comfort management, comprising:
    monitoring an aircraft occupant seated in an aircraft occupant seat in an aircraft, substantially around the aircraft occupant seat for health, safety, alertness/sleepiness, and comfort information using at least one first sensor disposed in the aircraft occupant seat and using at least one second sensor disposed substantially around the aircraft occupant seat;
    measuring background electrical noise, audible noise, and mechanical vibration associated with the aircraft occupant seat using at least one third sensor disposed in the aircraft occupant seat;
    obtaining the health, safety and comfort information associated with the aircraft occupant using the monitored health, safety and comfort information and the measured background electrical noise, audible noise and mechanical vibration; and
    managing health, safety and comfort of the aircraft occupant based on the obtained health, safety and comfort information.

2. The method of claim 1, wherein managing health, safety and comfort of the aircraft occupant, comprises:
    sending an alert to crew, by displaying the health, safety and comfort information on a cabin display device, sending an alert to other aircraft occupants residing in the cabin, sending an alert to off board aircraft occupant medical monitoring facility via satellite/ground station based on the obtained health, safety and comfort information, and/or sending the health, safety and comfort information to the crew or the off board aircraft occupant medical monitoring facility based on phase of operation of the aircraft.

3. The method of claim 2, wherein managing health, safety and comfort of the aircraft occupant, further comprises:
    receiving instructions from the off board aircraft occupant medical monitoring facility via the satellite/ground station by aircraft network data processing system to manage health, safety, and comfort of the aircraft occupant.

4. The method of claim 3, wherein the instructions received from the aircraft occupant medical monitoring facility includes at least one of first aid instructions, prescription information, and suggesting landing the aircraft.

5. The method of claim 1, wherein the at least one first sensor and the at least one third sensor is a contact-free/air gap sensor.

6. The method of claim 5, wherein the at least one first and the at least one third sensor is selected from the group consisting of piezoelectric sensor, electric potential measurement sensor, optical fiber Bragg grating sensor, and wherein the at least one second sensor is a cabin condition sensor.

7. The method of claim 1, wherein the at least one first and the at least one third sensor is disposed in the aircraft occupant seat, headrest to accommodate varying sizes and positions of the aircraft occupant.

8. The method of claim 1, wherein the at least one first sensor is used for measuring vital signs of the aircraft occupant.

9. The method of claim 1, wherein the at least one first sensor is used for measuring chest muscle movement/breathing rate of the aircraft occupant.

10. The method of claim 1, wherein the at least one second sensor is used for measuring ambient condition around the aircraft occupant seated in the aircraft occupant seat and substantially around the aircraft occupant seat.

11. The method of claim 1, wherein management of the health, safety and comfort to the aircraft occupant comprises adjusting airflow vent/air conditioner temperature substantially around the occupant seat based, providing ability to obtain waiting position number for washroom and informing the aircraft occupant about availability of the washroom upon reaching the obtained waiting position number, notifying seat belt condition to the aircraft occupant, providing a timed/scheduled blue/green light to the aircraft occupant based on directed light to nerve receptors behind eyes/temple or ears to help aircraft occupant wakeup gradually, providing an optimized seating position to the aircraft occupant, providing appropriate audio level to the aircraft occupant, switching off audio/pausing the in flight entertainment system on detecting sleep, providing appropriate refreshments to the aircraft occupant, providing seat presence or absence signal to cabin crew, providing ambient noise cancellation or white noise to the aircraft occupant, providing emergency equipment condition information to the cabin-crew, and/or providing condition of personal electronic equipment connected to the aircraft occupant based on the obtained health, safety, background electrical noise and comfort information.

12. The method of claim 1, further comprising:
    providing ability to turn-on and turn-off the aircraft network data processing system for monitoring the health, safety and comfort information by the aircraft occupant.

13. A system for aircraft occupant health, safety and comfort management, comprising:
    cabin environmental systems;
    a cabin display;
    at least one first sensor, wherein the at least one first sensor comprises of cabin condition sensors;
    an aircraft network and communication system communicatively coupled to the cabin environmental systems, the cabin display and the at least one first sensor;
    a ground station computing system communicatively coupled to the aircraft network and communication system via a satellite/ground station; and
    an aircraft occupant seat comprises:
        an aircraft occupant seat health, safety and comfort management system, wherein the aircraft occupant seat health, safety and comfort management system, comprises:
            at least one processor;
            a network interface card to couple to the aircraft network and communication system;
            at least one second sensor and at least one third sensor disposed in the aircraft occupant seat; and memory coupled to the at least one processor, wherein the memory comprises an aircraft occupant health, safety and comfort management module (AOHSCMM) to:
  monitor an aircraft occupant, seated in an aircraft occupant seat in an aircraft, substantially around the aircraft occupant seat for health, safety, alertness/sleepiness and comfort information using the at least one second sensor disposed in the aircraft occupant seat and using the at least one first sensor disposed substantially around the aircraft occupant seat;
  measure background electrical noise, audible noise and mechanical vibration associated with the aircraft occupant seat using the at least one third sensor;
  obtain the health, safety and comfort information associated with the aircraft occupant using the monitored health, safety and comfort information and the measured background electrical noise, audible noise and mechanical vibration; and
  provide health, safety and comfort management to the aircraft occupant based on the obtained health, safety and comfort information.

14. The system of claim 13, wherein the AOHSCMM sends an alert to crew by displaying the health, safety and comfort information on a cabin display device, sends an alert to other aircraft occupants residing in the cabin, sends an alert to off board aircraft occupant medical monitoring facility via satellite/ground station based on the obtained health, safety and comfort information, and/or sends the obtained health, safety and comfort information to the crew or the off board aircraft occupant medical monitoring facility based on phase of operation of the aircraft.

15. The system of claim 14, wherein the AOHSCMM and the aircraft network and communication system are configured to receive instructions from the off board aircraft occupant medical monitoring facility via the satellite/ground station by aircraft network data processing system to manage health, safety, and/or comfort of the aircraft occupant.

16. The system of claim 15, wherein the instructions received from the aircraft occupant medical monitoring facility includes at least one of first aid instructions, prescription information, and suggesting landing the aircraft.

17. The system of claim 13, wherein the at least one second sensor and the at least one third sensor is a contact-free/air gap sensor.

18. The system of claim 17, wherein the at least one second sensor and the at least one third sensor is selected from the group consisting of piezoelectric sensor, electric potential measurement sensor, and optical fiber Bragg grating sensor.

19. The system of claim 13, wherein the at least one second sensor and the at least one third sensor is disposed in the aircraft occupant seat, headrest to accommodate varying sizes and positions of the aircraft occupant.

20. The system of claim 13, wherein the at least one second sensor is used for measuring vital signs of the aircraft occupant.

21. The system of claim 13, wherein the at least one second sensor is used for measuring chest muscle movement, sensing pulse of the aircraft occupant.

22. The system of claim 13, wherein management of the health, safety and comfort to the aircraft occupant comprises adjusting airflow vent/air conditioner temperature substantially around the occupant seat based, providing ability to obtain waiting position number for washroom and informing the aircraft occupant about availability of the washroom upon reaching the obtained waiting position number, notifying seat belt condition to the aircraft occupant, providing a timed/scheduled blue/green light to the aircraft occupant to help aircraft occupant wakeup gradually, providing an optimized seating position to the aircraft occupant, providing appropriate audio level to the aircraft occupant, switching off audio/pausing the in flight entertainment system on detecting sleep, providing appropriate refreshments to the aircraft occupant, providing seat presence or absence signal to cabin-crew, providing ambient noise cancellation or white noise to the aircraft occupant, providing emergency equipment condition information to the cabin-crew, and/or providing condition of personal electronic equipment connected to the aircraft occupant based on the obtained health, safety, background electrical noise and comfort information.

23. The system of claim 13, wherein the AOHSCMM is configured to turn-on and turn-off the aircraft network and communication system for monitoring of the health, and comfort information by the aircraft occupant.

24. The system of claim 13, wherein the at least one first sensor is used for measuring ambient condition around the aircraft occupant seated in the aircraft occupant seat and substantially around the aircraft occupant seat.

* * * * *